(12) United States Patent
Dalton

(10) Patent No.: US 7,311,712 B2
(45) Date of Patent: *Dec. 25, 2007

(54) POLYAXIAL LOCKING SCREW PLATE ASSEMBLY

(75) Inventor: Brian E. Dalton, Erie, PA (US)

(73) Assignee: Aesculap Implant Systems, Inc., Center Valley, PA (US)

( * ) Notice: Subject to any disclaimer, the term of this patent is extended or adjusted under 35 U.S.C. 154(b) by 159 days.

This patent is subject to a terminal disclaimer.

(21) Appl. No.: 10/788,098

(22) Filed: Feb. 26, 2004

(65) Prior Publication Data

US 2005/0192580 A1    Sep. 1, 2005

(51) Int. Cl.
*A61B 17/80* (2006.01)
*A61B 17/86* (2006.01)

(52) U.S. Cl. .......................... 606/71; 606/73

(58) Field of Classification Search .............. 606/69, 606/73, 61, 70–72
See application file for complete search history.

(56) References Cited

U.S. PATENT DOCUMENTS

| | | | |
|---|---|---|---|
| 4,463,753 A | 8/1984 | Gustilo | |
| 4,484,570 A | 11/1984 | Sutter et al. | |
| 5,129,899 A | 7/1992 | Small et al. | |
| 5,147,363 A | 9/1992 | Härle | |
| 5,211,647 A * | 5/1993 | Schmieding | 606/104 |
| 5,269,784 A * | 12/1993 | Mast | 606/69 |
| 5,486,176 A | 1/1996 | Hildebrand et al. | |
| 5,520,690 A | 5/1996 | Errico et al. | |
| 5,531,746 A | 7/1996 | Errico et al. | |
| 5,540,690 A | 7/1996 | Miller et al. | |
| 5,607,426 A | 3/1997 | Ralph et al. | |
| 5,620,443 A | 4/1997 | Gertzbein et al. | |
| 5,643,265 A * | 7/1997 | Errico et al. | 606/70 |
| 5,669,911 A | 9/1997 | Errico et al. | |
| 5,735,853 A | 4/1998 | Olerud | |
| 5,749,916 A | 5/1998 | Richelsoph | |
| 5,797,911 A | 8/1998 | Sherman et al. | |
| 5,800,433 A | 9/1998 | Benzel et al. | |
| 5,863,293 A | 1/1999 | Richelsoph | |
| 5,876,402 A | 3/1999 | Errico et al. | |
| 5,879,350 A | 3/1999 | Sherman et al. | |
| 5,885,286 A | 3/1999 | Sherman et al. | |
| 5,954,635 A | 9/1999 | Foley et al. | |
| 5,954,722 A | 9/1999 | Bono | |
| 5,964,760 A | 10/1999 | Richelsoph | |
| 5,976,187 A | 11/1999 | Richelsoph | |
| 6,022,350 A | 2/2000 | Ganem | |
| 6,030,389 A | 2/2000 | Wagner et al. | |
| 6,033,406 A | 3/2000 | Mathews | |

(Continued)

*Primary Examiner*—Eduardo C. Robert
*Assistant Examiner*—Richard Shaffer
(74) *Attorney, Agent, or Firm*—RatnerPrestia

(57) ABSTRACT

A bone fixation assembly includes a fixation device, a cup shaped bushing, and a fastening screw. The fixation device has a through passage with an annular recess. The a fastening screw has a threaded shaft for insertion through the through passage and for threadable insertion into bone. The screw has a head with substantially frustospherical shaped side surfaces and mates with the cup shaped bushing. The annular recess in the through passage of the fixation device is configured and dimensioned to downwardly, directly, and annularly receive an upper end of the bushing under compression with a snap fit to prevent the screw from backing out of the bone fixation assembly.

5 Claims, 4 Drawing Sheets

U.S. PATENT DOCUMENTS

| | | | |
|---|---|---|---|
| 6,053,917 A | 4/2000 | Sherman et al. | |
| 6,074,391 A | 6/2000 | Metz-Stavenhagen et al. | |
| 6,083,225 A | 7/2000 | Winslow et al. | |
| 6,096,038 A | 8/2000 | Michelson | |
| 6,132,432 A | 10/2000 | Richelsoph | |
| 6,146,386 A | 11/2000 | Blackman et al. | |
| 6,152,871 A | 11/2000 | Foley et al. | |
| 6,159,179 A | 12/2000 | Simonson | |
| 6,162,170 A | 12/2000 | Foley et al. | |
| 6,171,311 B1 | 1/2001 | Richelsoph | |
| 6,197,033 B1 | 3/2001 | Haid, Jr. et al. | |
| 6,200,322 B1 | 3/2001 | Branch et al. | |
| 6,206,822 B1 | 3/2001 | Foley et al. | |
| 6,217,509 B1 | 4/2001 | Foley et al. | |
| 6,235,033 B1 | 5/2001 | Brace et al. | |
| 6,248,105 B1 * | 6/2001 | Schlapfer et al. | 606/61 |
| 6,261,291 B1 | 7/2001 | Talaber et al. | |
| 6,280,442 B1 | 8/2001 | Barker et al. | |
| 6,280,445 B1 | 8/2001 | Morrison et al. | |
| 6,287,311 B1 | 9/2001 | Sherman et al. | |
| 6,290,703 B1 | 9/2001 | Ganem | |
| 6,299,616 B1 | 10/2001 | Beger | |
| 6,328,738 B1 | 12/2001 | Suddaby | |
| 6,328,740 B1 | 12/2001 | Richelsoph | |
| 6,328,741 B1 | 12/2001 | Richelsoph | |
| 6,331,179 B1 | 12/2001 | Freid et al. | |
| RE37,665 E | 4/2002 | Ralph et al. | |
| 6,402,752 B2 | 6/2002 | Schäffler-Wachter et al. | |
| 6,402,756 B1 | 6/2002 | Ralph et al. | |
| 6,428,542 B1 | 8/2002 | Michelson | |
| 6,451,021 B1 | 9/2002 | Ralph et al. | |
| 6,514,260 B1 | 2/2003 | Zdeblick et al. | |
| 6,520,907 B1 | 2/2003 | Foley et al. | |
| 6,527,776 B1 | 3/2003 | Michelson | |
| 6,530,929 B1 | 3/2003 | Justis et al. | |
| 6,533,786 B1 | 3/2003 | Needham et al. | |
| 6,562,046 B2 | 5/2003 | Sasso | |
| 6,565,565 B1 | 5/2003 | Yuan et al. | |
| 6,575,899 B1 | 6/2003 | Foley et al. | |
| 6,575,975 B2 | 6/2003 | Brace et al. | |
| 6,599,290 B2 | 7/2003 | Bailey et al. | |
| 6,602,255 B1 | 8/2003 | Campbell et al. | |
| 6,623,485 B2 | 9/2003 | Doubler et al. | |
| 6,645,207 B2 | 11/2003 | Dixon et al. | |
| 6,663,616 B1 | 12/2003 | Roth et al. | |
| 6,682,534 B2 | 1/2004 | Patel et al. | |
| 6,695,772 B1 | 2/2004 | Bon et al. | |
| 6,695,846 B2 | 2/2004 | Richelsoph et al. | |
| 6,712,818 B1 | 3/2004 | Michelson | |
| 6,712,819 B2 | 3/2004 | Zucherman et al. | |
| 6,780,185 B2 | 8/2004 | Frei et al. | |
| 6,780,186 B2 | 8/2004 | Errico et al. | |
| 2001/0034521 A1 | 10/2001 | Bailey et al. | |
| 2001/0037111 A1 | 11/2001 | Dixon et al. | |
| 2002/0161368 A1 | 10/2002 | Foley et al. | |
| 2002/0183754 A1 | 12/2002 | Michelson | |
| 2003/0045875 A1 | 3/2003 | Bertranou | |
| 2003/0060826 A1 | 3/2003 | Foley et al. | |
| 2003/0073996 A1 | 4/2003 | Doubler et al. | |
| 2003/0149431 A1 | 8/2003 | Varieur | |
| 2003/0208203 A1 | 11/2003 | Lim et al. | |
| 2003/0216735 A1 | 11/2003 | Altarac et al. | |
| 2004/0039384 A1 | 2/2004 | Boehm, Jr. et al. | |
| 2004/0127897 A1 | 7/2004 | Freid et al. | |
| 2004/0133207 A1 | 7/2004 | Abdou | |

* cited by examiner

POLYAXIAL LOCKING SCREW PLATE ASSEMBLY

BACKGROUND OF THE INVENTION

This invention relates generally to a spinal implant assembly for holding adjacent vertebral bones fixed. More particularly, the present invention pertains to a spinal plate assembly which includes a mechanism for fixedly attaching and locking bone fixation screws to the plate at desired angles and for preventing back out of the screws from the plate.

SUMMARY OF THE INVENTION

The bone fixation assembly of the present invention includes a fixation device such as a plate having a through passage for receiving a bone fixation screw therethrough into bone in order to secure the plate to the bone. The assembly further includes a bushing having an annular cup shaped side wall with upper and lower ends and which defines an upwardly open interior bowl for receiving a screw head which has substantially frustospherical shaped side surfaces. Annularly spaced slots are provided in the side wall and depend downwardly from the upward end of the bowl for allowing inward compression of the side wall at the upper end of the bushing. A centrally located screw shank passage is provided in the lower end of the bushing to permit passage of the screw shank, but prevent passage of the screw head.

The bowl of the bushing is configured and dimensioned for polyaxial rotation of the screw head therein and for preventing back out of the screw head when the side wall of the bushing is compressed inwardly around the screw head. The through passage of the fixation device or plate is further configured and dimensioned to downwardly receive the bushing with the screw head contained therein for thereby inwardly compressing the bushing about the screw head. An annular recess is provided in the through passage and is configured and dimensioned to annularly receive the upper end of the bushing under compression with a snap fit whereby the screw head is retained in the bowl and is thereby prevented from backing out.

In another embodiment of the present invention, the bone fixation screw is provided with a screw head that is expandable for thereby locking the screw relative to the assembly. The screw head is split into segments at its upper or lower end and an expanding mechanism is received in the screw head between segments for expanding the segments outward.

The device for expanding the segments of the screw head includes an expansion screw centrally received in the screw head and a cam mechanism disposed between the expansion screw and the segmented screw head for expanding the screw head upon axially rotation of the expansion screw. In one embodiment this cam mechanism includes radially extending cam ramps. In yet another embodiment the cam mechanism includes axially extending cam ramps. For example with this latter embodiment, the cam ramps may include tapered sides on the expansion screw.

BRIEF DESCRIPTION OF THE DRAWINGS

Other objects and advantages appear hereinafter in the following description and claims. The accompanying drawings show, for the purpose of exemplification, without limiting the scope of the invention or appended claims, certain practical embodiments of the present invention wherein:

DETAILED DESCRIPTION OF THE PREFERRED EMBODIMENTS

Figure 3:
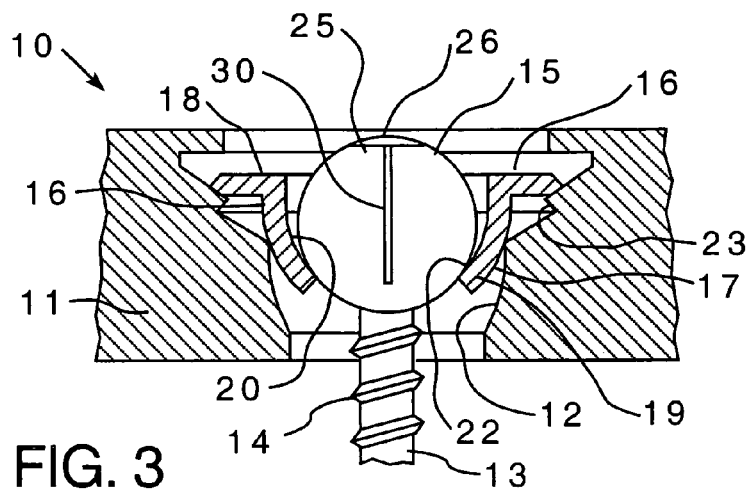
FIGS. 3, 4 and 5 are schematic sequence drawings illustrating the application of the bone fixation assembly of the present invention.
Figure 4:
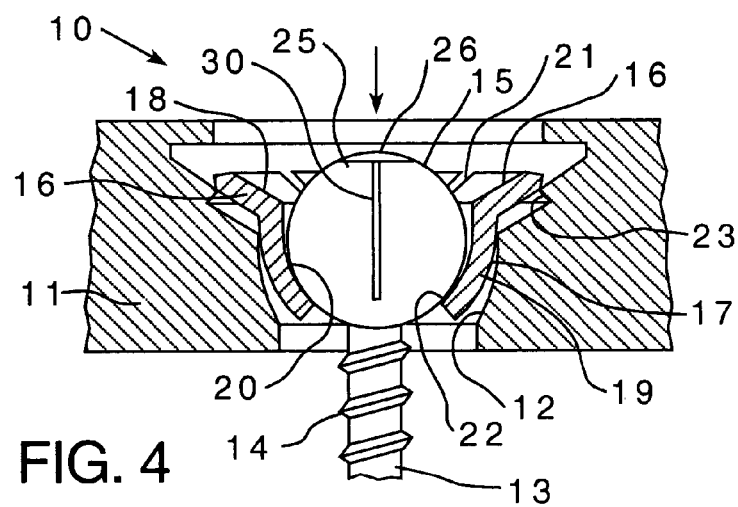
Figure 5:
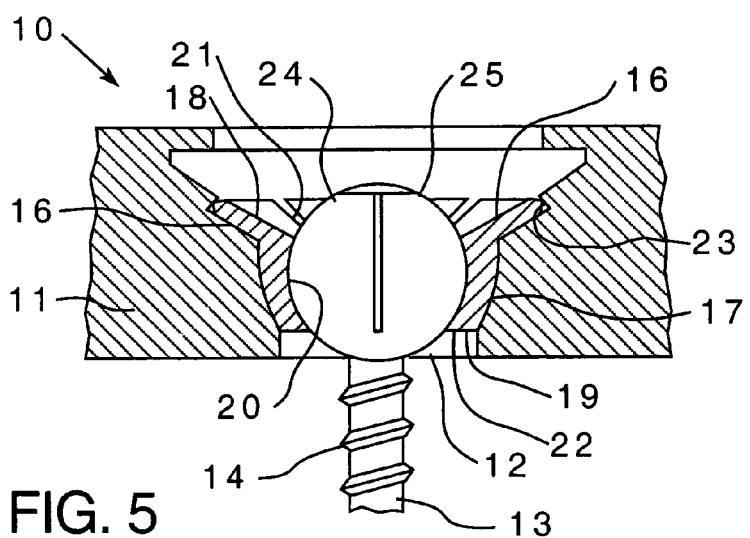

Referring first to sequence application FIGS. 3, 4 and 5, the bone fixation assembly 10 is illustrated. The bone fixation assembly 10 includes a fixation device 11, here illustrated as a bone fixation plate, having a through passage 12 and a fastening screw 13 having a threaded shaft 14 for insertion through the through passage 12 and threadable insertion into underlying bone (not shown). Screw 13 is further provided with head 15 having substantially frustospherical shaped side surfaces.

Figure 1:
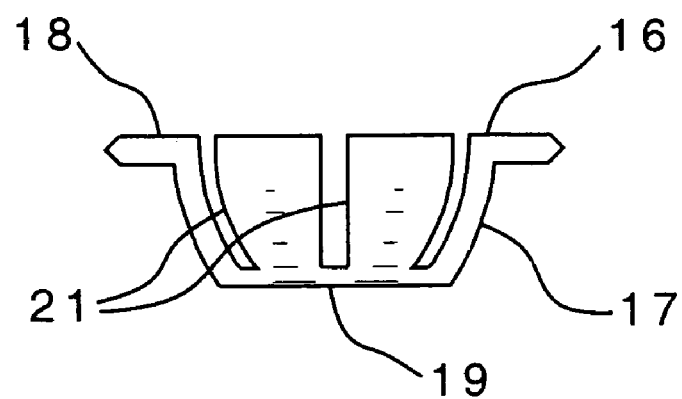
FIG. 1 is a view in front elevation of the bushing utilized in the bone fixation assembly of the present invention.
Figure 2:
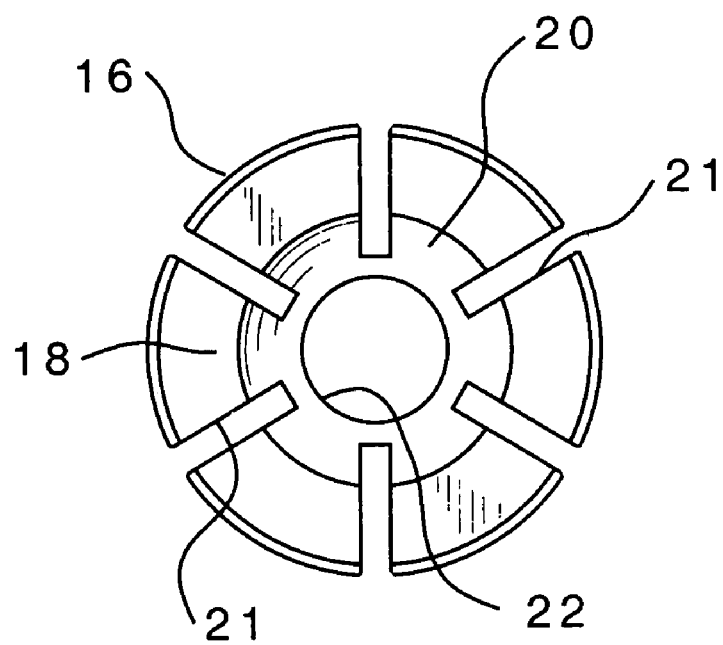
FIG. 2 is a top or plan view of the bushing shown in FIG. 1.

A bushing 16, which is also shown in detail in FIGS. 1 and 2, is provided and has an annular shaped side wall 17 having upper and lower ends 18 and 19 respectively. The side wall 17 defines an upwardly open interior bowl 20 for receiving screw head 15 therein. Annularly spaced slots 21 are provided in side wall 17 and depend downwardly from the upper end 18 for allowing inward compression of side wall 17 at upper end 18. A centrally located screw shank passage 22 is provided in the lower end 19 of bushing 16 for passage of screw shank 13 but not screw head 15.

Bowl 20 is configured and dimensioned for polyaxial rotation of screw head 15 therein and for preventing back out of the screw head when the side wall 17 is compressed inwardly about screw head 15 as is illustrated in FIG. 5. As is illustrated in FIGS. 3, 4 and 5, the through passage 12 is configured and dimensioned to downwardly receive the bushing therein as progressively illustrated in the three figures and represented by the downward arrow in FIG. 4 for thereby inwardly compressing bushing 16 about screw head 15 as is illustrated in the final representation of FIG. 5. An annular recess 23 is provided in through passage 12 and is configured and dimensioned to annularly receive the upper end 18 of bushing 16 under compression with a snap fit as is illustrated in FIG. 5 whereby the screw head 15 is retained in bowl 20 and is thereby prevented from backing out.

Figures 6, 7:
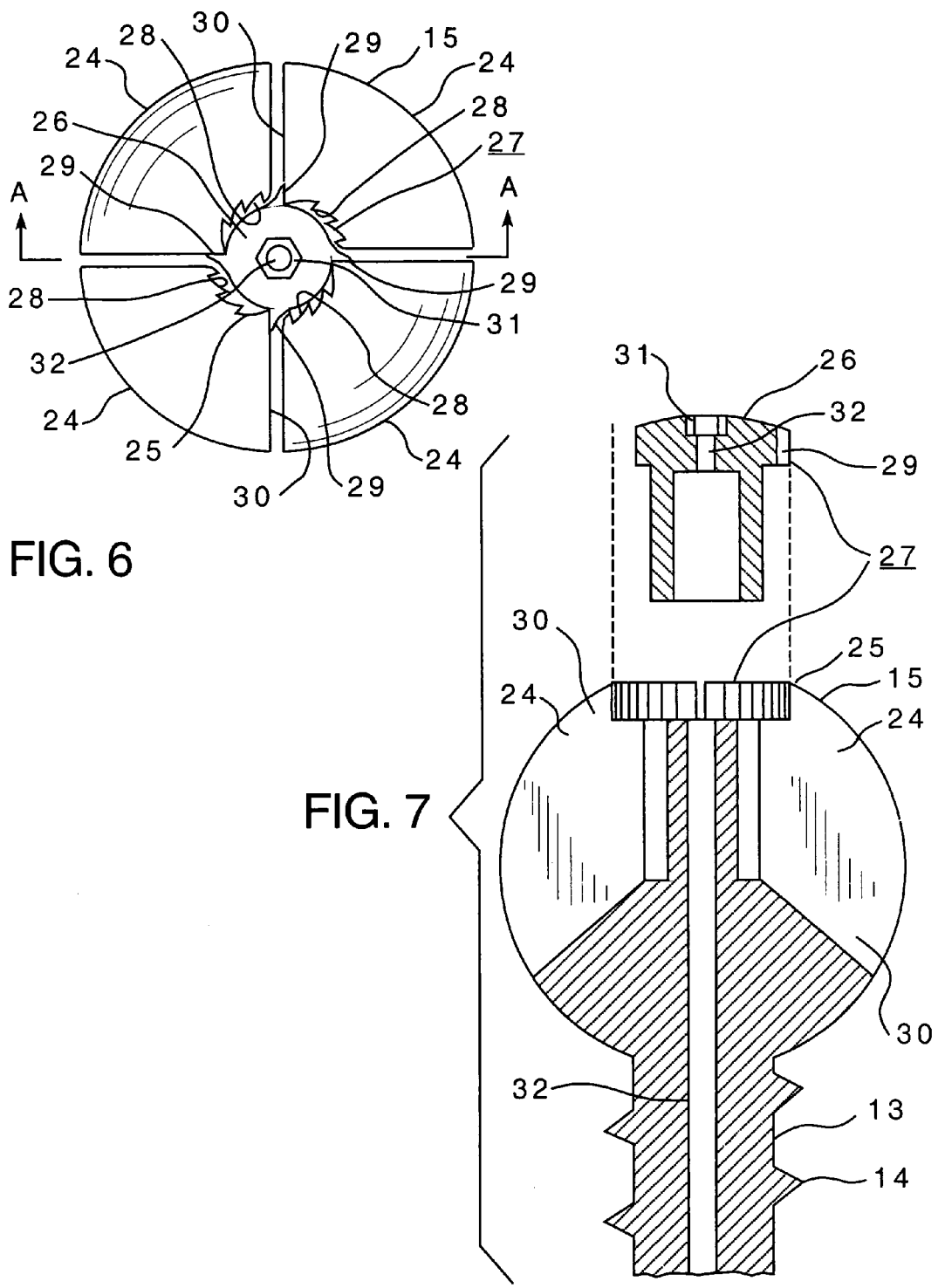
FIG. 6 is an enlarged top view of the bone fixation screw shown in FIGS. 3, 4 and 5.
FIG. 7 is an exploded view in side elevation of the bone fixation screw shown in FIG. 6 as seen along section line A-A.

The detail of bone screw 13 is illustrated in FIGS. 6 and 7. As previously indicated, screw head 15 has substantially frustospherical shaped side surfaces and is split into four segments 24 at the upper end of screw head 15 by slots 30 whereby screw head 15 is radially expandable at its upper end 25. More or fewer segments are also permissible. An expansion pawl 26 is centrally and slidably received in the upper end 25 of screw head 15 for rotation, and a cam mechanism 27 is disposed between expansion pawl 26 and segmented screw head 15 for expanding screw head 15 upon axial rotation of expansion pawl 26.

As may be best seen in FIG. 6, the upper end 25 of screw head 15 is provided with multiple radially extending cam steps 28 for each of the head segments 24 and these cam steps 28 are provided in the form of teeth with intervening ramps that progressively converge inwardly toward expansion pawl 26 as one progresses in the counterclockwise direction. This cam mechanism 27 further includes four cam followers 29 radially protruding outwardly from the upper end of expansion pawl 26. These followers 29 are engaged against the respective segments 24 of screw head 15 and they are so prepositioned in the slots 30 providing segments 24 whereby when expansion pawl 26 is rotated clockwise by a screwdriver engaging the hex drive cavity 31 of the upper end of expansion pawl 26, the entire screw head 15 together with its threaded shaft 13 is rotated clockwise for driving the screw shank 14 downwardly into underlying bone.

Once the bone fixation screw 13 is fully secured as illustrated in FIG. 5, the outer expandable portion of the screw head 15 is stabilized with the outer Phillips-drive sleeve of a screwdriver (not shown), rotation of the expansion pawl 26 is advanced in a counterclockwise direction by an inner drive of the screwdriver whereby the cam followers 29 will progressively engage the cam steps 28 of each corresponding head segment 24. As these followers 29 progressively engage the cam steps 28, the upper end of head 15 is annularly expanded to thereby lock the screw 13 from further polyaxial rotation within the bowl 20 of bushing 16. The cam followers 29 and the cam steps 28 are configured and dimensioned whereby full expansion and locking of the screw head within the assembly 10 is accomplished with less than a quarter counterclockwise turn of the expansion pawl 26.

The bone fixation screw 13 is fully cannulated as illustrated by the central cannulation passage 32 to permit the use of guide wires during the surgical procedure.

Figure 8:
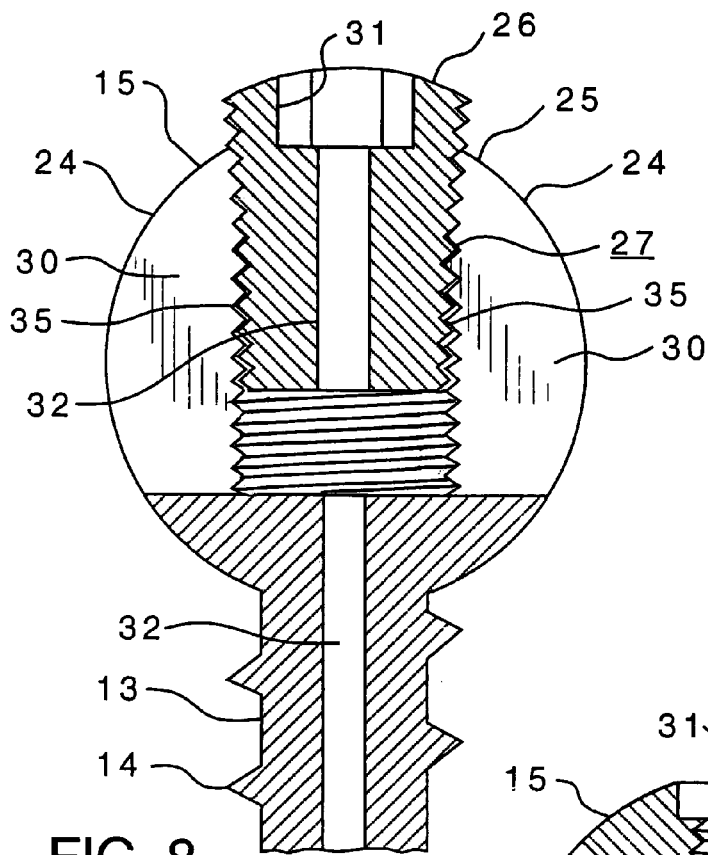
FIG. 8 is an enlarged view shown in vertical mid cross section illustrating another embodiment of the bone fixation screw shown in the previous figures.

Turning next to FIG. 8, another embodiment of the screw 13 is illustrated wherein the expandable head 15 is here expanded by the cam mechanism 27 which includes axially extending cam ramps 35, as opposed to radially extending cam ramps shown in the illustration of FIGS. 6 and 7. Here the axially extending cam ramps are in the form of tapered sides on expansion screw 26.

Figure 9:
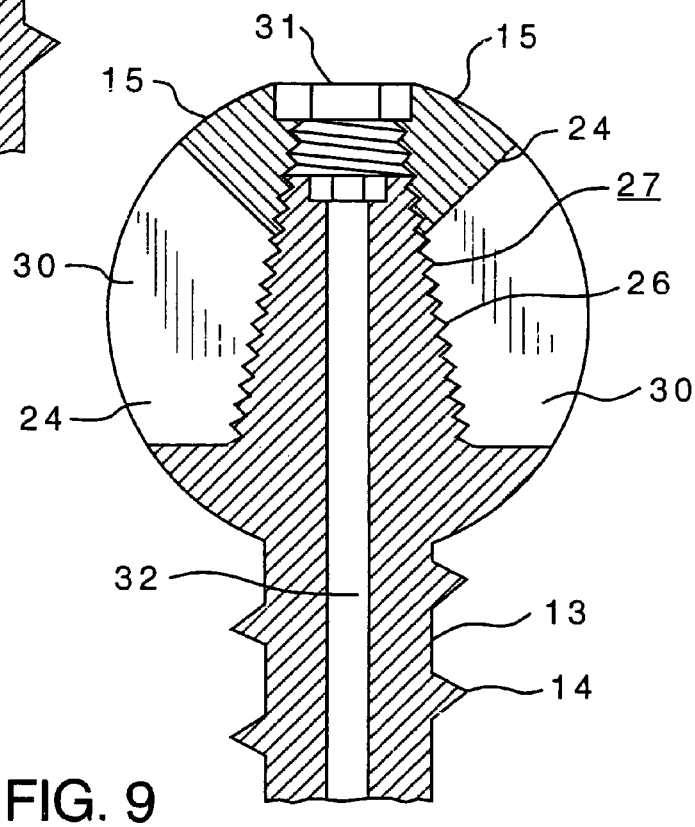
FIG. 9 is an enlarged view in vertical mid cross section illustrating yet another embodiment of the bone fixation screw of the present invention.

Yet another embodiment is illustrated in FIG. 9 in which head 15 is segmented at the bottom end thereof instead of at the top, and the cam mechanism 27 includes an expansion screw 26 which in this instance is secured to the upper end of screw shank 13 and is also provided with tapered sides to thereby expand the four segments 24 of screw head 15 at the bottom end thereof to lock the screw head 15 from further polyaxial rotation.

I claim:
1. A bone fixation assembly comprising:
(a) a fixation device having a through passage;
(b) an annular recess in said through passage;
(c) a fastening screw having a threaded shaft for insertion through said through passage and threadable insertion into bone, and a head having substantially frustospherical shaped side surfaces;
(d) a bushing having:
(i) an annular cup shaped side wall having upper and lower ends and defining an upwardly open interior bowl for receiving said screw head, said upper end of said side wall having a first circumference when said bushing is not engaged with said annular recess of said through passage, and a second, smaller circumference when said bushing is engaged with said annular recess of said through passage;
(ii) annularly spaced slots in said side wall which depend downwardly from said upper end for allowing inward compression of said side wall at said upper end;
(iii) a centrally located screw shank passage in said lower end;
(iv) said bowl configured and dimensioned for polyaxial rotation of said screw head therein and for preventing back out of said screw head when said side wall is compressed inwardly; and
(e) said fixation device through passage configured and dimensioned to downwardly receive said bushing therein to inwardly compress said upper end of said side wall of said bushing about said screw head,
wherein said annular recess in said through passage is configured and dimensioned to annularly and directly receive said upper end of said annular cup shaped side wall of said bushing under compression with a snap fit when said upper end of said annular cup shaped side wall of said bushing is at said second circumference whereby said screw head is retained in said bowl and prevented from backing out.

2. The bone fixation assembly of claim 1 wherein said screw head is expandable for thereby locking said screw relative to said assembly.

3. The bone fixation assembly of claim 2, further comprising an expansion means, wherein said screw head is split into segments at its upper or lower end, and the expansion means is received in said screw head between segments for expanding said segments.

4. The bone fixation assembly of claim 3 wherein said expansion means includes radially extending cam ramps.

5. The bone fixation assembly of claim 3 wherein said fastening screw and said expansion means are axially cannulated for receiving a guide wire.

* * * * *